(12) United States Patent
Pretz et al.

(10) Patent No.: US 11,613,506 B2
(45) Date of Patent: *Mar. 28, 2023

(54) CHEMICAL PROCESSES AND SYSTEMS THAT INCLUDE THE COMBUSTION OF SUPPLEMENTAL FUELS

(71) Applicant: Dow Global Technologies LLC, Midland, MI (US)

(72) Inventors: Matthew T. Pretz, Lake Jackson, TX (US); Hangyao Wang, Pearland, TX (US); Lin Luo, Sugarland, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/496,308

(22) Filed: Oct. 7, 2021

(65) Prior Publication Data
US 2022/0024838 A1    Jan. 27, 2022

Related U.S. Application Data

(63) Continuation of application No. 17/256,688, filed as application No. PCT/US2019/039216 on Jun. 26, 2019, now Pat. No. 11,203,559.

(60) Provisional application No. 62/694,196, filed on Jul. 5, 2018.

(51) Int. Cl.
*C07C 5/333*         (2006.01)

(52) U.S. Cl.
CPC ........ *C07C 5/3337* (2013.01); *C07C 2523/62* (2013.01)

(58) Field of Classification Search
CPC ... C07C 5/3337; C07C 2523/62; C07C 11/06; C07C 2521/04; C07C 2521/08;
(Continued)

(56) References Cited

U.S. PATENT DOCUMENTS 3,033,906 A * 5/1962 Hay .................. C07C 5/412
                                                    585/420
3,657,153 A * 4/1972 Bucur et al. .......... C10G 35/09
                                                    502/262
(Continued)

FOREIGN PATENT DOCUMENTS

EP          637578 A1    2/1995
WO         0156960 A1    8/2001
(Continued)

OTHER PUBLICATIONS

U.S. Office Action dated Mar. 18, 2022 pertaining to U.S. Appl. No. 17/256,690, filed Dec. 29, 2020, 12 pages.
(Continued)

*Primary Examiner* — Thuan D Dang
(74) *Attorney, Agent, or Firm* — Dinsmore & Shohl LLP

(57) ABSTRACT

According to one or more embodiments presently disclosed, a method for processing a chemical stream may include contacting a feed stream with a catalyst in a reactor portion of a reactor system that includes a reactor portion and a catalyst processing portion. Contacting the feed stream with the catalyst may cause a reaction forming an effluent. The method may include separating the effluent stream from the catalyst, passing the catalyst to the catalyst processing portion, and processing the catalyst in the catalyst processing portion. Processing the catalyst may include passing the catalyst to a combustor, combusting a supplemental fuel stream in the combustor to heat the catalyst, and treating the heated catalyst with an oxygen-containing gas. The supplemental fuel stream may include at least 1 mol % of one or more hydrocarbons, and a weight ratio of catalyst to hydrocarbons in the combustor may be at least 300:1.

17 Claims, 5 Drawing Sheets

(58) Field of Classification Search
CPC .. C07C 2523/08; C07C 2523/42; Y02P 20/52; Y02P 20/584; B01J 23/62
See application file for complete search history.

(56) References Cited

U.S. PATENT DOCUMENTS

| | | | |
|---|---|---|---|
| 4,072,600 | A | 2/1978 | Schwartz |
| 7,595,427 | B2 | 9/2009 | Sanfilippo et al. |
| 8,653,317 | B2 | 2/2014 | Pierce et al. |
| 8,669,406 | B2 | 3/2014 | Pretz et al. |
| 9,815,040 | B2 | 11/2017 | Pretz et al. |
| 9,827,543 | B2 | 11/2017 | Pretz et al. |
| 9,834,496 | B2 | 12/2017 | Pretz et al. |
| 10,065,905 | B2 | 9/2018 | Pretz et al. |
| 2004/0029715 | A1 | 2/2004 | Schindler et al. |
| 2004/0259727 | A1 | 12/2004 | Bartolini et al. |
| 2010/0004118 | A1 | 1/2010 | Liu et al. |
| 2010/0236985 | A1 | 9/2010 | Luo et al. |
| 2011/0269620 | A1 | 11/2011 | Myers et al. |
| 2013/0137909 | A1 | 5/2013 | Dean et al. |
| 2014/0200385 | A1 | 7/2014 | Pretz et al. |
| 2014/0378731 | A1 | 12/2014 | Iezzi et al. |
| 2016/0060542 | A1 | 3/2016 | Sugita et al. |
| 2016/0152901 | A1 | 6/2016 | Dufresne |
| 2017/0087528 | A1 | 3/2017 | Pretz et al. |

FOREIGN PATENT DOCUMENTS

| | | |
|---|---|---|
| WO | 02096844 A1 | 12/2002 |
| WO | 2005077867 A2 | 8/2005 |
| WO | 2010107591 A1 | 9/2010 |
| WO | 2013009820 A1 | 1/2013 |
| WO | 2016160273 A1 | 10/2016 |
| WO | 2017151361 A1 | 9/2017 |

OTHER PUBLICATIONS

U.S. Office Action dated Oct. 13, 2021 pertaining to U.S. Appl. No. 17/256,690, filed Dec. 29, 2020, 20 pages.
Sadeghbeigi, R., Fluid Catalytic Cracking Handbook, Third Edition, Chapter 10: pp. 197-219 (Year: 2012).
Notice of Allowance and Fee(s) Due dated Apr. 13, 2022, pertaining to U.S. Appl. No. 17/256,706, 13 pgs.
Examination Report pertaining to corresponding G.C.C. Patent Application No. 2019-37879, dated Apr. 29, 2020.
Examination Report pertaining to corresponding G.C.C. Patent Application No. 2019-37879, dated Jul. 15, 2020.
International Search Report and Written Opinion pertaining to PCT/US2019/039209, dated Oct. 2, 2019.
International Search Report and Written Opinion pertaining to PCT/US2019/039212, dated Oct. 1, 2019.
International Search Report and Written Opinion pertaining to PCT/US2019/039216, dated Oct. 9, 2019.
Deutschmann, et al., Hydrogen assisted catalytic combustion of methane on platinum; Catalysis Today, 2000, 59(1-2), 141-150.
Warnatz, et al., A model of elementary chemistry and fluid mechanics in the combustion of hydrogen on platinum surfaces; Combustion and Flame, (1994), 96(4), 393-406.
Rinnemo, et al., Experimental and numerical investigation of the catalytic ignition of mixtures of hydrogen and oxygen on platinum Combustion and Flame, (1977), 111(4), 312-326.
Tiernan, et al., Effects of ceria on the combustion activity and surface properties of Pt/Al2O3 catalysts; Applied Catalysis, B. Environmental, (1998), 19(1), 23-35.
Ikeda, et al., Surface kinetics for catalytic combustion of hydrogen-air mixtures on platinum at atmospheric pressure in stagnation flows; Surface Science, (1995), 326(1/2), 11-26.
U.S. Office Action dated Dec. 21, 2021 pertaining to U.S. Appl. No. 17/256,690, filed Dec. 29, 2020, 5 pages.
U.S. Office Action dated Dec. 21, 2001 pertaining to U.S. Appl. No. 17/256,706, filed Dec. 29, 2020, 21 pages.
U.S. Office Action dated Aug. 26, 2022 pertaining to U.S. Appl. No. 17/256,690, filed Dec. 29, 2020, pp. 1-11.
English Translation of Argentia Substantive Examination Report pertaining to AR Patent Application No. 20190101925, 4 pgs.
English Translation of Argentia Substantive Examination Report pertaining to AR Patent Application No. 20190101924, 3 pg.

\* cited by examiner

CHEMICAL PROCESSES AND SYSTEMS THAT INCLUDE THE COMBUSTION OF SUPPLEMENTAL FUELS

CROSS-REFERENCE TO RELATED APPLICATIONS

This application is a continuation of U.S. patent application Ser. No. 17/256,688, filed Dec. 29, 2020, which is a National Stage Entry under 35 U.S.C. § 371 of International Patent Application No. PCT/US2019/039216, filed Jun. 26, 2019, which claims priority to U.S. Provisional Patent Application Ser. No. 62/694,196, filed on Jul. 5, 2018, the entire disclosures of which are hereby incorporated by reference.

BACKGROUND

Field

The present disclosure generally relates to chemical processing systems and the operation thereof and, more specifically, to processes in which processing the catalyst includes combusting a supplemental fuel stream.

Technical Background

Light olefins may be utilized as base materials to produce many types of goods and materials. For example, ethylene may be utilized to manufacture polyethylene, ethylene chloride, or ethylene oxides. Such products may be utilized in product packaging, construction, textiles, etc. Thus, there is an industry demand for light olefins, such as ethylene, propylene, and butene.

Light olefins may be produced by different reaction processes depending on the given chemical feed stream, such as a product stream from a crude oil refining operation. Many light olefins may be produced through various catalytic processes, such as through catalytic dehydrogenation for example, in which the feed stream is contacted with a fluidized catalyst that facilitates conversion of the feed stream into the light olefins.

BRIEF SUMMARY

There is a continued need for improved processes for reactor systems for processing chemical streams to produce light olefins or other chemical products. In particular, the processes may include improved methods for heating the catalyst through combustion of supplemental fuel sources. Many reactor systems for processing chemical streams to produce light olefins and other chemicals utilize relatively hot catalyst, such as those catalysts heated to temperatures greater than 350° C. The catalyst may be circulated through fluidized reactor systems, such as through a reactor portion (where chemical products are made) and through a catalyst processing portion (in which the catalyst is processed, such as but not limited to removal of coke, heating of the catalyst, reactivating the catalyst, other catalyst processing operations, or combinations of these).

In endothermic fluidized reactor systems, the reactor system includes a heat source to drive the process. For example, in fluidized catalytic cracking ("FCC") reactions, coke generated by the reaction and deposited on the catalyst may be combusted in a combustor of the catalyst processing portion to provide a major portion of the heat to drive the reaction process. However, some reaction processes for producing light olefins are endothermic and require heat input into the system to propagate the catalytic reactions and provide for the other heat demands in the system. Coke deposits on the catalyst may be combusted during catalyst processing, but the heat provided by combustion of coke deposits may not be sufficient to propagate the endothermic reactions. Supplemental fuels may be introduced during catalyst regeneration to increase the heat input into the reaction system.

For example, as another non-limiting embodiment, in fluidized catalytic dehydrogenation (FCDh) reactor systems, a supplemental fuel may be added to the combustor to provide the heat for the endothermic reaction along with combustion of a relatively small amount of coke from the reaction. Supplemental fuels may include significant proportions of methane and/or other hydrocarbons due to the affordable cost of methane and its energy efficiency at relatively high temperatures, such as those of the catalyst during operation (e.g., temperatures above 650° C.). However, combustion of supplemental fuels that include mainly methane and other hydrocarbons (e.g., greater than or equal to 50 mol % methane and other hydrocarbons) during catalyst processing may lead to reduced activity of the catalyst, such as a catalyst that includes platinum, gallium, or both for example.

The reduced activity of the catalysts can decrease the conversion that can be attained by the catalyst. In some fluidized reactor systems that utilize supplemental fuels that include mainly methane and other hydrocarbons, productivity of the reactor system may be maintained by increasing the amount of the catalyst in the reactor system or increasing the amount of active metal, such as platinum, gallium, or both, in the catalyst. However, increasing the amount of active metal, such as platinum, gallium, or both, in the reactor system can increase the operating costs of the reactor system.

Therefore, there is an ongoing need for reactor systems and processes that increase the conversion of a chemical feed by reducing deactivation of the catalyst. In particular, there is an ongoing need for reactor systems and methods that include combusting supplemental fuels and reduce the extent of deactivation of the catalysts during the combustion process prior to reactivation of the catalyst, thereby increasing catalyst activity. The present disclosure, according to one or more embodiments, is directed to processes and reactor systems that include combusting a supplemental fuel stream having one or more hydrocarbons (e.g., methane, natural gas, etc.) in a combustor to heat the catalyst. The weight ratio of catalyst to hydrocarbon in the combustor may be at least 300:1 during combustion of the supplemental fuel stream. Following combustion, the catalyst may be subjected to an oxygen treatment that includes exposing the catalyst to an oxygen-containing gas for a time sufficient to reactive the catalyst.

It was surprisingly and unexpectedly found that operating the combustor with a relatively high weight ratio of catalyst to hydrocarbons in the supplemental fuel stream (e.g., greater than or equal to 300:1) can result in greater catalyst dehydrogenation activity of the catalyst and an increase in the conversion of the reactor system compared to operating the combustor with a weight ratio of catalyst to hydrocarbons in the supplemental fuel of less than 300:1 under the same operating conditions (including the same oxygen treatment following combustion). Additionally, operating the combustor with a relatively high weight ratio of catalyst to hydrocarbons in the supplemental fuel stream (e.g., ≥300:1) can result in a catalyst with longer catalyst lifetime and may enable a target conversion to be achieved with less bulk inventory of catalyst in the reactor system compared to the bulk inventory of catalyst required to achieve the same target conversion when the weight ratio of catalyst to hydrocarbons in the combustor is relatively low (e.g., ≤300:1). In some embodiments, operating the combustor with a relatively high weight ratio of catalyst to hydrocarbons (e.g., ≥300:1) may enable the reactor system to be operated with less active metal, such as platinum, gallium, or both, on the catalyst or a more aged catalyst compared to reactor systems operated at lower weight ratios of catalyst to hydrocarbon in the combustor.

According to one or more aspects of the present disclosure, a method for dehydrogenating a feed stream to produce one or more olefin products may include contacting the feed stream with a catalyst in a reactor portion of a reactor system. The reactor system may include a fluidized catalytic dehydrogenation reactor system having a reactor portion and a catalyst processing portion. The catalyst may include platinum, gallium, or both. The contacting of the feed stream with the catalyst may cause a reaction which forms an effluent stream comprising the one or more olefin products. The method may further include separating at least a portion of the effluent stream from the catalyst, passing the catalyst to the catalyst processing portion of the reactor system, and processing the catalyst in the catalyst processing portion of the reactor system. Processing the catalyst may include passing the catalyst to a combustor of the catalyst processing portion, combusting a supplemental fuel stream in the combustor to heat the catalyst, and treating the heated catalyst with an oxygen-containing gas (oxygen treatment) to produce a reactivated catalyst. The supplemental fuel stream may include at least 1 mol % of one or more hydrocarbons, and a weight ratio of the catalyst to the one or more hydrocarbons in the combustor may be at least 300:1. The method may further include passing the reactivated catalyst from the catalyst processing portion to the reactor portion of the reactor system.

It is to be understood that both the foregoing brief summary and the following detailed description present embodiments of the technology, and are intended to provide an overview or framework for understanding the nature and character of the technology as it is claimed. The accompanying drawings are included to provide a further understanding of the technology, and are incorporated into and constitute a part of this specification. The drawings illustrate various embodiments and, together with the description, serve to explain the principles and operations of the technology. Additionally, the drawings and descriptions are meant to be merely illustrative, and are not intended to limit the scope of the claims in any manner.

Additional features and advantages of the technology disclosed herein will be set forth in the detailed description which follows, and in part will be readily apparent to those skilled in the art from that description or recognized by practicing the technology as described herein, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
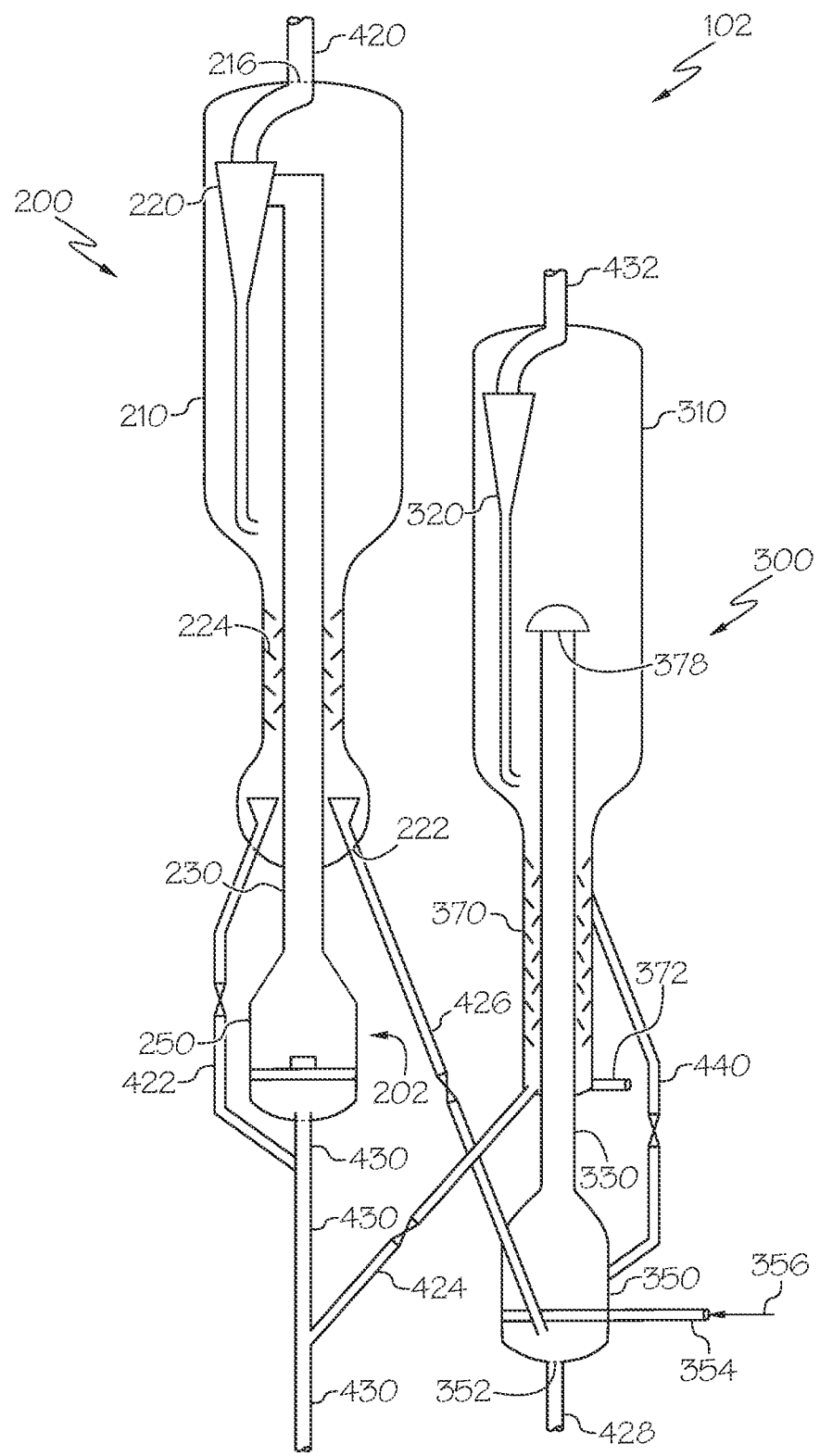
FIG. 1 schematically depicts a reactor system, according to one or more embodiments described herein.

It should be understood that the drawings are schematic in nature, and do not include some components of a reactor system commonly employed in the art, such as, without limitation, temperature transmitters, pressure transmitters, flow meters, pumps, valves, and the like. It would be known that these components are within the spirit and scope of the present embodiments disclosed. However, operational components, such as those described in the present disclosure, may be added to the embodiments described in this disclosure.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Several embodiments of the present disclosure are described in the detailed description which follows. The present disclosure is directed to methods for processing chemical streams in reactor systems utilizing a supplemental fuel stream to heat the catalyst. In particular, the present disclosure is directed to methods for dehydrogenating a feed stream to produce one or more olefin products in which a supplemental fuel stream that includes one or more hydrocarbons is combusted at a relatively high catalyst to hydrocarbon weight ratio (e.g., >300:1) in a catalyst processing portion of the reactor system to at least partially heat the catalyst. The method for dehydrogenating a feed stream to produce one or more olefin products may include contacting a feed stream with a catalyst in a reactor portion of a reactor system. The reactor system may include a fluidized catalytic dehydrogenation reactor system having a reactor portion and a catalyst processing portion. The catalyst may include platinum, gallium, or both. The contacting of the feed stream with the catalyst may cause a reaction which forms an effluent stream comprising the one or more olefin products. The method may further include separating at least a portion of the effluent stream from the catalyst, passing the catalyst to the catalyst processing portion of the reactor system, and processing the catalyst in the catalyst processing portion of the reactor system. Processing the catalyst may include passing the catalyst to a combustor of the catalyst processing portion, combusting a supplemental fuel stream in the combustor to heat the catalyst, and treating the heated catalyst with an oxygen-containing gas to produce a reactivated catalyst. The supplemental fuel stream may include at least 1 mol % of one or more hydrocarbons, and a weight ratio of the catalyst to the one or more hydrocarbons in the combustor may be at least 300:1. The method may further include passing the reactivated catalyst from the catalyst processing portion to the reactor portion of the reactor system.

Operating the combustor of the reactor system at a weight ratio of the catalyst to the hydrocarbon of greater than or equal to 300:1 during combustion of the supplemental fuel stream to heat the catalyst during catalyst processing was found to increase the conversion of reactants in the reactor system compared to operating the combustor at weight ratios of catalyst to hydrocarbon less than 300:1. This high catalytic activity of the catalyst may result in increased catalyst lifetime in the reactor system and may enable increasing the unit capacity of the reactor system. The higher catalyst activity resulting from maintaining a weight ratio of catalyst to hydrocarbon in the combustor of greater than or equal to 300:1 may enable the reactor system to operate with less active metal, such as platinum, gallium, or both, in the reactor system (e.g., less bulk inventory of catalyst, less active metal in the catalyst, utilization of more aged catalyst, or combinations thereof).

As used herein, the term "fluidized reactor system" refers to a reactor system in which one or more reactants are contacted with a catalyst in a fluidization regime, such as bubbling regime, slug flow regime, turbulent regime, fast fluidization regime, pneumatic conveying regime, or combinations thereof in different portions of the reactor system. For example, in a fluidized reactor system, a feed stream containing one or more reactants may be contacted with the circulating catalyst at an operating temperature to conduct a continuous reaction to produce the product stream.

As used herein, "continuous reaction" may refer to a chemical reaction conducted by feeding reactants, catalyst, or combinations thereof, and withdrawing products from a reactor or reaction zone under substantially steady state conditions continuously over a time period, which is defined by a commencement of the reaction at the beginning of the time period and a cessation of the reaction at the end of the time period. Thus, operation of the reactor systems described herein may include commencement of the reaction, continuous reaction, and cessation of the reaction.

As used herein, "deactivated catalyst" may refer to a catalyst having decreased catalytic activity resulting from buildup of coke and/or loss of catalyst active sites.

As used herein, "catalytic activity" or "catalyst activity" may refer to the degree to which the catalyst is able to catalyze the reactions conducted in the reactor system.

As used herein, "catalyst processing" may refer to preparing the catalyst for re-introduction into the reactor portion of the reactor system and may include removing coke deposits from the catalyst, heating the catalyst, reactivating the catalyst, stripping one or more constituents from the catalyst, other processing operations, or any combinations of these.

As used herein, "processed catalyst" may refer to catalyst that has been processed in the catalyst processing portion of the reactor system.

As used herein, "catalyst reactivation" or "reactivating the catalyst" may refer to processing the catalyst that has been at least partially deactivated to restore at least a portion of the catalyst activity to produce a reactivated catalyst. The catalyst that has been at least partially deactivated may be reactivated by, but not limited to, recovering catalyst acidity, oxidizing the catalyst, other reactivation process, or combinations thereof. For example, in some embodiments, catalyst reactivation may include treating the catalyst with an oxygen-containing gas for a period of greater than 2 minutes.

As used herein, "supplemental fuel" may refer to any fuel source introduced to the catalyst processing portion of the reactor system to facilitate removing coke from the catalyst and/or heating the catalyst. Supplemental fuel does not include coke deposited on the catalyst.

As previously discussed herein, according to one or more embodiments, the methods and processes disclosed herein may be utilized to conduct a reaction in a reactor system for processing one or more chemical streams. In non-limiting examples, the reactor systems disclosed herein may be utilized to produce light olefins from hydrocarbon feed streams through continuous reaction of the hydrocarbon feed streams with a dehydrogenation catalyst. For example, in some embodiments, light olefins may be produced through dehydrogenation of a hydrocarbon feed stream in the presence of a catalyst that includes platinum, gallium, or both in a fluidized catalytic dehydrogenation (FCDh) reactor system. While the processes and methods for processing a chemical stream in a reactor system are described herein in the context of hydrocarbon processing to form light olefins through fluidized catalytic dehydrogenation, it should be understood that the processes and methods disclosed herein may be utilized with any reactor system that includes a catalyst having an active metal, such as platinum, gallium, other active metal, or combinations of these, and that includes heating the catalyst by combustion of a supplemental fuel. As such, the presently described methods and processes for processing a chemical stream in a reactor system may not be limited only to embodiments for reactor systems designed to produce light olefins or alkyl aromatics through fluidized catalytic dehydrogenation, such as the reactor system in FIG. 1.

The reactor systems and methods for processing the chemical streams will now be discussed in further detail. The chemical stream that is processed may be referred to as a feed stream, which is processed by a reaction to form a product stream. The feed stream may comprise a composition, and depending upon the feed stream composition, an appropriate catalyst may be utilized to convert the contents of the feed stream into a product stream that may include light olefins or other chemical products. For example, a feed stream for a FCDh reactor system may comprise at least one of propane, n-butane, iso-butane, ethane, or ethylbenzene. In the FCDh system, the feed stream may be converted to light olefins or other products through dehydrogenation in the presence of a dehydrogenation catalyst.

In some embodiments, the catalyst for conducting dehydrogenation in an FCDh reactor system may include a catalyst comprising platinum, gallium, or both. In some embodiments, the catalyst may further include one or more noble metals from Groups 9 and 10 of the IUPAC periodic table. For example, in some embodiments, the catalyst may include one or more noble metals chosen from palladium (Pd), rhenium (Rh), iridium (Ir), or combinations of these. In some embodiments, the catalyst may also include one or more metals chosen from indium (In), germanium (Ge), or combinations of these. The catalyst may also include a promoter metal, such as an alkali metal or an alkaline metal. In some embodiments, the promoter metal may be potassium. The metals of the catalyst may be supported on a carrier. The carrier may include one or more inorganic bulk metal oxides, such as silica, alumina, silica-containing alumina, zirconia ($ZrO_2$), titania ($TiO_2$), other metal oxides, or combinations of metal oxides. In some embodiments, the carrier may include a microporous material, such as ZSM-5 zeolite. The catalytic metals, such as platinum, gallium, potassium, and/or other catalytically active metals, may be supported on the surface of the carrier or incorporated into the carrier. In some embodiments, the catalyst may include platinum, gallium, and optionally potassium supported on a silica-containing alumina carrier.

Referring now to FIG. 1, an example reactor system 102 is schematically depicted. The reactor system 102 generally includes a reactor portion 200 and a catalyst processing portion 300. As used herein in the context of FIG. 1, the reactor portion 200 refers to the portion of a reactor system 102 in which the major process reaction takes place. For example, the reactor system 102 may be a FCDh reactor system in which the feed stream is dehydrogenated in the presence of the dehydrogenation catalyst in the reactor portion 200 of the reactor system 102. The reactor portion 200 comprises a reactor 202 which may include a downstream reactor section 230, an upstream reactor section 250, and a catalyst separation section 210, which serves to separate the catalyst from the chemical products formed in the reactor 202.

Also, as used herein, the catalyst processing portion 300 of the system of FIG. 1 generally refers to the portion of a reactor system 102 in which the catalyst is in some way processed, such as removing coke deposits, heating of the catalyst, reactivating the catalyst, other processing operations, or combinations of these. In some embodiments, the catalyst processing portion 300 may include a combustor 350, a riser 330, a catalyst separation section 310, and an oxygen treatment zone 370. The combustor 350 of the catalyst processing portion 300 may include one or more lower combustor inlet ports 352 and may be in fluid communication with the riser 330. The combustor 350 may be in fluid communication with the catalyst separation section 210 via standpipe 426, which may supply deactivated catalyst from the reactor portion 200 to the catalyst processing portion 300 for catalyst processing (e.g., coke removal, heating, reactivating, etc.). The oxygen treatment zone 370 may be in fluid communication with the upstream reactor section 250 (e.g., via standpipe 424 and transport riser 430), which may supply processed catalyst from the catalyst processing portion 300 back to the reactor portion 200. The combustor 350 may include an additional lower combustor inlet port 352 where air inlet 428 connects to the combustor 350. The air inlet 428 may supply air or other reactive gases, such as an oxygen-containing gas to the combustor 350. Air and/or other reactive gases may be introduced to the combustor 350 to aid in combustion of the supplemental fuel stream. The combustor 350 may also include a supplemental fuel inlet 354. The supplemental fuel inlet 354 may supply a supplemental fuel stream 356 to the combustor 350. The oxygen treatment zone 370 may include an oxygen-containing gas inlet 372, which may supply an oxygen-containing gas to the oxygen treatment zone 370 for oxygen treatment of the catalyst.

Referring to FIG. 1, in some embodiments, the catalyst processing portion 300 may include a combustor catalyst recycle 440. In some embodiments, the combustor catalyst recycle 440 may fluidly couple the catalyst separation section 310 or the oxygen treatment zone 370 to the combustor 350. Thus, the catalyst separation section 310 or the oxygen treatment zone 370 may be in fluid communication with the combustor 350 via the combustor catalyst recycle 440 to pass heated or reactivated catalyst back to the combustor 350. The combustor catalyst recycle 440 may include a control device (not shown) operable to control a recycle rate of the catalyst from the catalyst separation section 310 or oxygen treatment zone 370 back to the combustor 350. In some embodiments, the heated catalyst may be recycled from the catalyst separation section 310 back to the combustor 350 before being reactivated in the oxygen treatment zone 370. In other embodiments, the reactivated catalyst from the oxygen treatment zone 370 may be recycled back to the combustor 350 after reactivation in the oxygen treatment zone 370.

Referring to FIG. 1, general operation of the reactor system 102 to conduct a continuous reaction will be described. During operation of the reactor portion 200 of the reactor system 102, the feed stream may enter the transport riser 430, and the product stream may exit the reactor system 102 via pipe 420. According to one or more embodiments, the reactor system 102 may be operated by feeding a chemical feed (e.g., in a feed stream) and a fluidized catalyst into the upstream reactor section 250. The chemical feed may contact the catalyst in the upstream reactor section 250, and each may flow upwardly into and through the downstream reactor section 230 to produce a chemical product. The chemical product and the catalyst may be passed out of the downstream reactor section 230 to a separation device 220 in the catalyst separation section 210. The catalyst may be separated from the chemical product in the separation device 220. The chemical product may then be transported out of the catalyst separation section 210. For example, the separated vapors may be removed from the reactor system 102 via a pipe 420 at a gas outlet port 216 of the catalyst separation section 210. According to one or more embodiments, the separation device 220 may be a cyclonic separation system, which may include two or more stages of cyclonic separation.

According to some embodiments, following separation from vapors in the separation device 220, the catalyst may generally move through the stripper 224 to the reactor catalyst outlet port 222 where the catalyst may be transferred out of the reactor portion 200 via standpipe 426 and into the catalyst processing portion 300. Optionally, the catalyst may also be transferred directly back into the upstream reactor section 250 via standpipe 422. In some embodiments, recycled catalyst from the stripper 224 may be premixed with processed catalyst from the catalyst processing portion 300 in the transport riser 430.

The separated catalyst may be passed from the catalyst separation section 210 to the combustor 350 of the catalyst processing portion 300. The catalyst may be processed in the catalyst processing portion 300 to remove coke deposits, heat the catalyst, reactivate the catalyst, other catalyst processing, or any combinations of these. As previously discussed, processing the catalyst in the catalyst processing portion 300 may include removing coke deposits from the catalyst, raising the temperature of the catalyst through combustion of combustion fuel source, reactivating the catalyst, stripping one or more constituents from the catalyst, other processing operation, or combinations of these. In some embodiments, processing the catalyst in the processing portion 300 may include combusting a combustion fuel source in the presence of the catalyst in the combustor 350 to remove coke deposits and/or heat the catalyst to produce a heated catalyst. The heated catalyst may be separated from the combustion gases in the catalyst separation portion 310. In some embodiments, the heated catalyst may then be reactivated by conducting an oxygen treatment of the heated catalyst. The oxygen treatment may include exposing the catalyst to an oxygen-containing gas for a period of time sufficient to reactivate the catalyst.

In some embodiments, the combustion fuel source may include coke or other contaminants deposited on the catalyst in the reactor portion 200 of the reactor system 102. In some reaction systems, the catalyst may be coked following the reactions in the reactor portion 200, and the coke may be removed from the catalyst by a combustion reaction in the combustor 350. For example, an oxidizer (such as air) may be fed into the combustor 350 via the air inlet 428.

However, as previously discussed, in some reaction systems, the coke and other contaminants deposited on the catalyst may not be sufficient to heat the catalyst to a temperature great enough to carry out the endothermic reactions in the reactor portion 200. Thus, the combustion fuel source may further include the supplemental fuel stream 356, which may be introduced to the combustor 350 through a supplemental fuel inlet 354. For example, the supplemental fuel stream 356 may be injected into the combustor 350 through the supplemental fuel inlet 354 and combusted to heat the catalyst to a temperature sufficient to conduct the endothermic reactions in the reactor portion 200 as well provide for the other heat demands in the entire system 102. In some embodiments, no coke may be formed on the catalyst such that all of the heat for raising the temperature of the catalyst and/or for other heat requirements of the system are provided by the supplemental fuel stream 356. In some embodiments, reactive gases, such as an oxygen-containing gas (e.g., air) or other oxidizer for example, may be introduced to the combustor 350 through lower combustor inlet port 352 and may react with the supplemental fuel of the supplemental fuel stream 356 to promote combustion of the supplemental fuel to heat the catalyst to produce a heated catalyst. As used herein, the term "heated catalyst" refers to the catalyst after heating through combustion of the supplemental fuel stream 356, the catalyst having a temperature greater than the catalyst passed from the catalyst separation section 210 to the catalyst processing portion 300 of the reactor system 102.

Referring to FIG. 1, the processed catalyst may be passed out of the combustor 350 and through the riser 330 to a riser termination separator 378, where the gas and solid components from the riser 330 may be at least partially separated. The vapor and remaining solids may be transported to a secondary separation device 320 in the catalyst separation section 310 where the remaining processed catalyst is separated from the gases from the catalyst processing (e.g., gases emitted by combustion of coke deposits and supplemental fuel). In some embodiments, the secondary separation device 320 may include one or a plurality of cyclone separation units, which may be arranged in series or in multiple cyclone pairs. The combustion gases from combustion of coke and/or the supplemental fuel stream 356 during processing of the catalyst or other gases introduced to the catalyst during catalyst processing may be removed from the catalyst processing portion 300 via a combustion gas outlet 432.

As previously discussed, processing the catalyst in the catalyst processing portion 300 of the reactor system 102 may include reactivating the catalyst. Combustion of the supplemental fuel stream 356 in the presence of the catalyst to heat the catalyst may further deactivate the catalyst. Thus, in some embodiments, the oxygen treatment to reactivate the catalyst may be conducted after combustion of the supplemental fuel stream 356 to heat the catalyst. Conditioning the heated catalyst by treating the heated catalyst with an oxygen-containing gas for a period of at least two minutes may reactivate the catalyst to produce a reactivated catalyst. The oxygen-containing gas may include an oxygen content of from 5 mole % to 100 mole % based on total molar flow rate of the oxygen-containing gas. In some embodiments, the catalyst may be reactivated by conditioning the catalyst through an oxygen treatment. Oxygen treatment of the catalyst may include maintaining the catalyst at a temperature of at least 660° C. while exposing the catalyst to a flow of an oxygen-containing gas for a period of time greater than two minutes and sufficient to produce a reactivated catalyst having a catalytic activity that is greater than the heated catalyst after being heated by combustion of the supplemental fuel stream 356.

Referring to FIG. 1, treatment of the heated catalyst with the oxygen-containing gas may be conducted in the oxygen treatment zone 370. In some embodiments, the oxygen treatment zone 370 may be disposed in a downstream portion of the catalyst separation portion 310 of the catalyst processing portion 300, such that the heated catalyst is separated from the combustion gases before being exposed to the oxygen-containing gas during the oxygen treatment. In some embodiments, the oxygen treatment zone 370 may include a fluid solids contacting device. The fluid solids contacting device may include baffles or grid structures to facilitate contact of the heated catalyst with the oxygen-containing gas. Examples of fluid solid contacting devices are described in further detail in U.S. Pat. Nos. 9,827,543 and 9,815,040, both of which are incorporated by reference herein in their entirety.

In some embodiments, processing the catalyst in the catalyst processing portion 300 of the reactor system 102 may further include stripping the oxygen-containing reactivated catalyst of molecular oxygen trapped within or between catalyst particles and physisorbed oxygen that is desorbable at a temperature of at least 660° C. The stripping step may include maintaining the oxygen-containing reactivated catalyst at a temperature of at least 660° C. and exposing the oxygen-containing reactivated catalyst to a stripping gas that is substantially free of molecular oxygen and combustible fuels for a period of time to remove the molecular oxygen from between particles and physisorbed oxygen that is desorbable at the temperature of at least 660° C. Further description of these catalyst reactivation processes are disclosed in U.S. Pat. No. 9,834,496, which is incorporated by reference in the present disclosure in its entirety.

Following processing of the catalyst, the processed catalyst may be passed from the catalyst processing portion 300 back into the reactor portion 200 via standpipe 424. For example, in some embodiments, the processed catalyst may be passed from the oxygen treatment zone 370 of the catalyst processing portion 300 to the upstream reactor section 250 via standpipe 424 and transport riser 430, where the processed catalyst may be further utilized in a catalytic reaction. Thus, in operation, the catalyst may cycle between the reactor portion 200 and the catalyst processing portion 300. In general, the processed chemical streams, including the feed streams and product streams may be gaseous, and the catalyst may be a fluidized particulate solid.

In some embodiments, the heated catalyst accumulated in the catalyst separation section 310 or the reactivated catalyst from the oxygen treatment zone 370 may be recycled back to the combustor 350 via the combustor catalyst recycle 440. The recycle rate of the catalyst back to the combustor 350 may be increased or decreased by manipulating the control device (not shown) in the combustor catalyst recycle 440. In some embodiments, the recycle rate of the catalyst from the catalyst separation section 310 or oxygen treatment zone 370 to the combustor 350 may be increased or decreased to increase or decrease the weight ratio of catalyst to hydrocarbon in the combustor 350. In some embodiments, the heated catalyst may be recycled back to the combustor 350 before being subjected to the oxygen treatment. In other embodiments, the reactivated catalyst from the oxygen treatment zone 370 may be recycled to the combustor 350 after being reactivated by the oxygen treatment.

Referring again to FIG. 1, according to one or more embodiments, processing the catalyst in the catalyst processing portion 300 may include passing the catalyst from the reactor portion 200 of the reactor system 102 to the combustor 350 of the catalyst processing portion 300, combusting the supplemental fuel stream 356 in the combustor 350 to heat the catalyst, subjecting the heated catalyst to an oxygen treatment in the oxygen treatment zone 370 to produce a reactivated catalyst, and passing the reactivated catalyst from catalyst processing portion 300 to the reactor portion 200. Combustion of the supplemental fuel stream 356 and/or coke deposits in the catalyst processing portion 300 may remove the coke deposits or other contaminants deposited on the catalyst, increase the temperature of the catalyst to an operating temperature range of the reactor portion 200, or both. For example, in some embodiments, combustion of the supplemental fuel stream 356 in the combustor 350 may increase the temperature of the catalyst to produce a heated catalyst. In some embodiments, coke deposits may not be formed on the catalyst during the reaction, and the supplemental fuel stream 356 may provide all of the heat in the combustor for raising the temperature of the catalyst to produce the heated catalyst.

In some embodiments, the supplemental fuel stream 356 may include one or more hydrocarbons. The one or more hydrocarbons may include hydrocarbons that comprise energy value upon combustion. In some embodiments, the hydrocarbon may include one or more hydrocarbons that are gases at the operating temperatures of the combustor 350 (i.e., 650° C. to 850° C.), such as but not limited to, alkanes, alkenes, aromatic hydrocarbons, or combinations of these. Examples of alkanes that may be included as a hydrocarbon in the supplemental fuel stream 356 may include, but are not limited to methane, ethane, propane, butane, isobutane, pentane, other alkanes, or combinations of these. Examples of alkenes (olefins) that may be included as a hydrocarbon of the supplemental fuel stream 356 may include, but are not limited to, ethylene, propylene, 1-butene, 2-butene, isobutene, other olefins, or combinations of these. Examples of aromatic hydrocarbons that may be included as a hydrocarbon in the supplemental fuel stream 356 may include, but are not limited to, benzene, toluene, xylene, other aromatic hydrocarbons, or combinations of these. In some embodiments, the hydrocarbons may include a light hydrocarbon (i.e., $C_1$-$C_4$) fuel gas. In other embodiments, the hydrocarbons may include heavy hydrocarbon based fuel oils ($C_{5+}$). In some embodiments, the hydrocarbon may include at least one of methane, ethane, propane, natural gas, other hydrocarbon fuel, or combinations of these. In some embodiments, the one or more hydrocarbons may include methane.

In some embodiments, the supplemental fuel stream 356 may include at least 1 mol % hydrocarbon based on the total molar flow rate of the supplemental fuel stream. For example, in some embodiments, the supplemental fuel stream 356 may include greater than or equal to 1 mol %, greater than or equal to 5 mol %, greater than or equal to 10 mol %, or greater than or equal to 15 mol % of one or more hydrocarbons based on the total molar flow rate of the supplemental fuel stream 356. In some embodiments, the supplemental fuel stream 356 may include from 1 mol % to 99 mol %, from 1 mol % to 70 mol %, from 1 mol % to 60 mol %, from 1 mol % to 50 mol %, from 1 mol % to 30 mol %, from 5 mol % to 99 mol %, from 5 mol % to 70 mol %, from 5 mol % to 60 mol %, from 5 mol % to 50 mol %, from 5 mol % to 30 mol %, from 10 mol % to 99 mol %, from 10 mol % to 70 mol %, from 10 mol % to 60 mol %, from 10 mol % to 50 mol %, or from 10 mol % to 30 mol % hydrocarbons based on the total molar flow rate of the supplemental fuel stream 356. Some hydrocarbon-based supplemental fuels, such as methane and natural gas for example, have a relatively high heat value and are inexpensive. Thus, in some embodiments, hydrocarbon fuels, such as methane and natural gas for example, may be utilized in the supplemental fuel stream 356 to reduce the operating costs of the reactor system 102. In other embodiments, the hydrocarbon may be present in an off-gas stream passed to the combustor 350 as at least a portion of the supplemental fuel stream 356, the off-gas stream originating from a hydrocarbon processing system.

In some embodiments, the supplemental fuel stream 356 may further include hydrogen. For example, in some embodiments, the supplemental fuel stream 356 may include greater than or equal to 50 mol % hydrogen, such as greater than or equal to 70 mol %, greater than or equal to 75 mol %, greater than or equal to 80 mol %, greater than or equal to 85 mol %, or greater than or equal to 90 mol % hydrogen, based on the total molar flow rate of the supplemental fuel stream 356. For example, in some embodiments, the supplemental fuel stream 356 may include from 40 mol % to 100 mol %, from 70 mol % to 100 mol %, from 70 mol % to 99 mol %, from 70 mol % to 95 mol %, from 70 mol % to 90 mol %, from 70 mol % to 85 mol %, from 75 mol % to 100 mol %, from 75 mol % to 99 mol %, from 75 mol % to 95 mol %, from 75 mol % to 90 mol %, from 75 mol % to 85 mol %, from 80 mol % to 100 mol %, from 80 mol % to 99 mol %, from 80 mol % to 95 mol %, from 80 mol % to 90 mol %, from 85 mol % to 100 mol %, from 85 mol % to 99 mol %, from 85 mol % to 95 mol %, or from 90 mol % to 100 mol % hydrogen based on the total molar flow rate of the supplemental fuel stream 356. In some embodiments, the supplemental fuel stream 356 may include greater than or equal to 25 wt. %, greater than or equal to 30 wt. %, greater than or equal to 35 wt. %, greater than or equal to 40 wt. %, or greater than or equal to 50 wt. % hydrogen based on the total mass flow rate of the supplemental fuel stream 356. For example, in some embodiments, the supplemental fuel stream may include from 25 wt. % to 100 wt. %, from 25 wt. % to 99 wt. %, from 25 wt. % to 95 wt. %, from 30 wt. % to 100 wt. %, from 30 wt. % to 99 wt. %, from 30 wt. % to 95 wt. %, from 35 wt. % to 100 wt. %, from 35 wt. % to 99 wt. %, from 35 wt. % to 95 wt. %, from 40 wt. % to 100 wt. %, from 40 wt. % to 99 wt. %, from 40 wt. % to 95 wt. %, from 50 wt. % to 100 wt. %, or from 50 wt. % to 99 wt. % hydrogen.

As previously discussed, the combustor 350 may be operated with a weight ratio of catalyst to hydrocarbon in the supplemental fuel stream of greater than or equal to 300:1, such as greater than or equal to 500:1, greater than or equal to 700:1, greater than or equal to 1000:1, or even greater than or equal to 1500:1. For example, in some embodiments, the weight ratio of catalyst to hydrocarbon in the combustor may be from 300:1 to 10,000:1, from 300:1 to 5000:1, from 300:1 to 2500:1, from 500:1 to 10,000:1, from 500:1 to 5000:1, from 500:1 to 2500:1, from 700:1 to 10000:1, from 700:1 to 5000:1, from 700:1 to 2500:1, from 1000:1 to 5000:1, or from 1500:1 to 5000:1.

It was surprisingly found that operating the combustor 350 of the catalyst processing portion 300 at a weight ratio of catalyst to hydrocarbon of greater than or equal to 300:1 can increase the conversion of the reactor system compared to operating the combustor 350 with a lower weight ratio of catalyst to hydrocarbon (e.g., ≤300:1).

Operating the combustor 350 at a weight ratio of catalyst to hydrocarbon of at least 300:1 may reduce the amount of deactivation that occurs to the active sites of the catalyst during combustion of the supplemental fuel stream 356 in the combustor 350. Thus, the heated catalyst produced by operating the combustor with a weight ratio of catalyst to hydrocarbon of greater than or equal to 300:1 may have a greater catalytic activity compared to catalyst heated in the combustor operated with a lower weight ratio of catalyst to hydrocarbon. Operating the combustor 350 at a weight ratio of catalyst to hydrocarbon of at least 300:1 may increase the lifetime of the catalyst in the reactor system 102. Further, operating the combustor 350 at a weight ratio of catalyst to hydrocarbon of at least 300:1 may also increase the capacity of the reactor system 102, such as by, but not limited to, increasing the conversion for a specific catalyst loading or reducing the catalyst loading required to achieve a target conversion, compared to operating the combustor 350 at a lesser weight ratio of catalyst to hydrocarbon. For example, in a reactor system 102 utilizing a catalyst comprising platinum, gallium, or both to dehydrogenate propane to produce propylene, operating the combustor 350 at a weight ratio of catalyst to hydrocarbon of at least 300:1 can result in the same conversion performance in the reactor system with less active metal (e.g., platinum, gallium, or both) compared to operating the operating the combustor 350 at a lesser weight ratio of catalyst to hydrocarbons. Operating the reactor system with less active metal (e.g., platinum, gallium, or both) may include operating with a reduced bulk inventory of catalyst in the reactor system or reducing the amount of active metal (e.g., platinum, gallium, or both) in the catalyst (e.g., using a catalyst having less active metal applied to the catalyst or using aged catalyst).

In some embodiments, the weight ratio of the catalyst to the hydrocarbon in the combustor 350 may be increased or decreased by modifying the type and concentrations of the fuel gases in the supplemental fuel stream 356, modifying the flow rate of the supplemental fuel stream 356, modifying the recycle rate of the catalyst from the catalyst separation section 310 or oxygen treatment zone 370 to the combustor 350, or combinations of these. For example, in some embodiments, the molar concentration of the hydrocarbons in the supplemental fuel stream 356 may be increased or decreased to decrease or increase, respectively, the weight ratio of catalyst to hydrocarbon in the combustor 350. For example, increasing the molar concentration of hydrocarbon in the supplemental fuel stream 356 may decrease the weight ratio of catalyst to hydrocarbon in the combustor 350. Conversely, decreasing the molar concentration of hydrocarbons in the supplemental fuel stream 356 may increase the weight ratio of catalyst to hydrocarbon in the combustor 350.

In some embodiments, the weight ratio of the catalyst to the hydrocarbons in the combustor 350 may be increased or decreased by decreasing or increasing, respectively, the flow rate of the supplemental fuel stream 356 to the combustor 350 at a constant feed rate of the catalyst to the combustor 350. For example, decreasing the flow rate of the supplemental fuel stream 356 while maintaining the catalyst feed rate to the combustor constant may increase the weight ratio of catalyst to hydrocarbon in the combustor 350.

In some embodiments, the weight ratio of the catalyst to hydrocarbon in the combustor 350 may be increased or decreased by modifying a recycle rate of the catalyst from the catalyst separation section 310 or oxygen treatment zone 370 to the combustor 350. For example, increasing the recycle rate of the catalyst to the combustor 350 may increase the weight ratio of catalyst to hydrocarbon in the combustor 350. Conversely, decreasing the recycle rate of the catalyst to the combustor 350 may decrease the weight ratio of catalyst to hydrocarbon in the combustor 350. In some embodiments, the combustor 350 may be operated under conditions of constant heat input. In these embodiments, the weight ratio of catalyst to hydrocarbon in the combustor 350 may be modified by increasing or decreasing the molar concentration of hydrocarbon in the supplemental fuel stream 356 and making a corresponding adjustment to the flow rate of the supplemental fuel stream 356 to maintain the heat input rate constant. Alternatively, under constant heat input conditions, the weight ratio of catalyst to hydrocarbon in the combustor 350 may be modified by increasing or decreasing the recycle rate of catalyst to the combustor 350 and maintaining the composition and flow rate of the supplemental fuel stream 356 constant.

In some embodiments, the supplemental fuel stream 356 may include a purity hydrogen stream comprising greater than or equal to 99 mol % hydrogen based on the total molar flow rate of the supplemental fuel stream. In some embodiments, the purity hydrogen stream may be combined with one or more streams comprising hydrocarbons to produce the supplemental fuel stream 356. In some embodiments, the supplemental fuel stream 356 may include process stream from a hydrocarbon processing plant. The process stream from a hydrocarbon processing plant/system may include greater than or equal to 50 mol %, greater than or equal to 60 mol %, greater than or equal to 70 mol %, greater than or equal to 80 mol %, or greater than or equal to 90 mol % hydrogen based on the total molar flow rate of the process stream. In some embodiments, the process stream from the hydrocarbon processing plant may be an off-gas stream. For example, in some embodiments, the supplemental fuel stream 356 may include an off-gas stream from a FCDh reactor system, such as but not limited to a propane dehydrogenation process for example, and/or an off-gas stream from a light hydrocarbon cracking process. It is understood that off-gas streams from other hydrocarbon processing systems having greater than or equal to 40 mol % hydrogen may also be utilized as or included in the supplemental fuel stream 356. In some embodiments, the supplemental fuel stream 356 may consist of or consist essentially of an off-gas stream from a hydrocarbon processing system. In other embodiments, the supplemental fuel stream 356 may include the off-gas stream in combination with one or more other fuel streams comprising hydrogen, a hydrocarbon component, or both.

Figure 2:
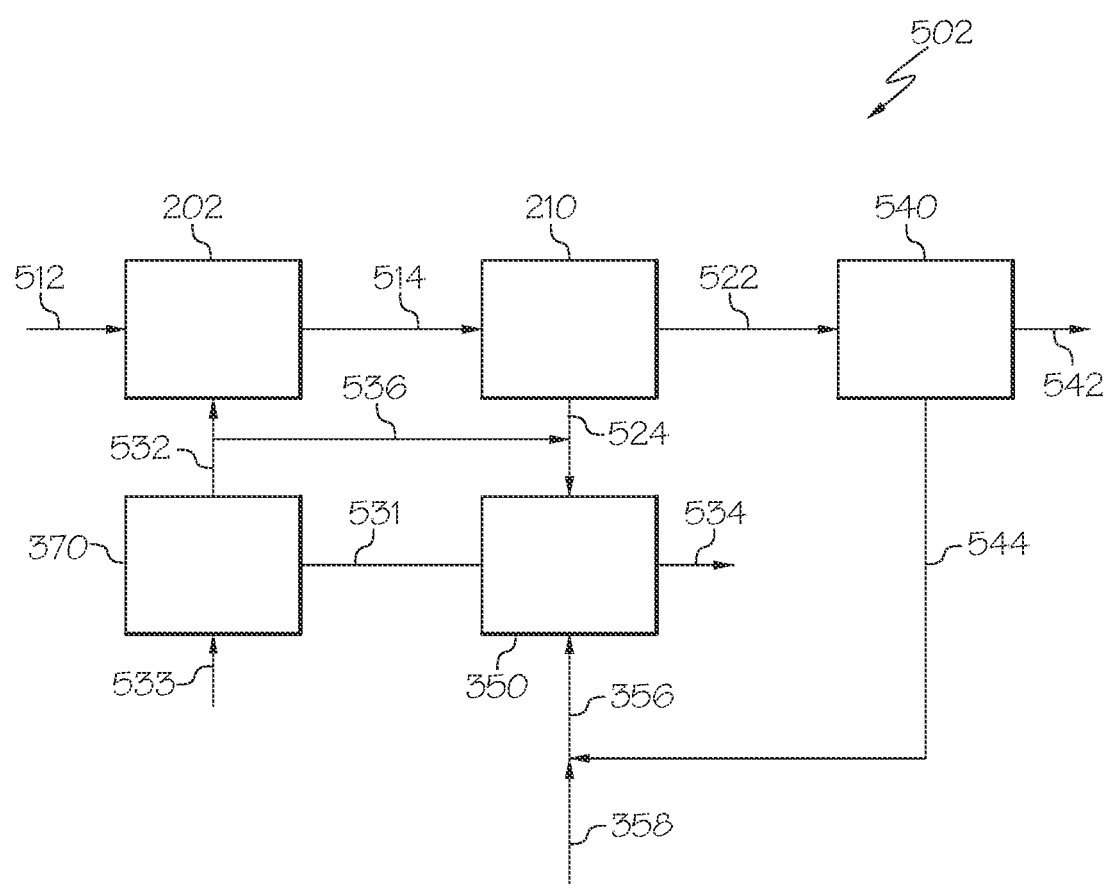
FIG. 2 schematically depicts a reactor system flow chart, according to one or more embodiments described herein.

Referring now to FIG. 2, a process flowchart of a FCDh process 502 for dehydrogenating hydrocarbons to produce olefins and other products (e.g., styrene from ethylbenzene) is depicted. In the FCDh process 502 of FIG. 2, an off-gas stream 544 from the dehydrogenation reaction may be passed to the combustor 350 to provide at least a portion of the supplemental fuel stream 356. The FCDh process 502 depicted in FIG. 2 may include the reactor system 102 depicted in FIG. 1. The FCDh process 502 may include the reactor 202, the catalyst separation section 210, the combustor 350, and the oxygen treatment zone 370. The FCDh process 502 may further include a product separator 540 downstream of the catalyst separation section 210.

During continuous operation of the FCDh process 502 of FIG. 2, a chemical feed 512 and the reactivated catalyst 532 from the oxygen treatment zone 370 may be introduced to the reactor 202. Contact of reactants in the chemical feed 512 with the reactivated catalyst 532 may convert a portion of reactants in the chemical feed 512 to one or more reaction products (e.g., ethylene, propylene, styrene, etc.) and by-products. A reactor effluent 514 may be passed from the reactor 202 to the catalyst separation section 210. The reactor effluent 514 may include at least catalyst, reaction products, and unreacted reactants from the chemical feed, but may also include by-products, intermediate compounds, impurities, carrier gases, or other constituents. The catalyst separation section 210 may separate the reactor effluent 514 into a gaseous effluent stream 522 and a deactivated catalyst stream 524. The gaseous effluent stream 522 may include at least reaction products and unreacted reactant gases. The deactivated catalyst stream 524 may be passed to the combustor 350 for at least a portion of the catalyst processing. In the combustor 350, the supplemental fuel stream 356 may be combusted in the presence of the deactivated catalyst stream 524 to remove coke from the catalyst, heat the catalyst, or both. Following combustion, the heated catalyst 531 may be separated from the combustion gases 534 and passed to the oxygen treatment zone 370. In the oxygen treatment zone 370, the heated catalyst 531 may be treated with an oxygen-containing gas 533 to produce the reactivated catalyst 532. The reactivated catalyst 532 may then be passed back to the reactor 202.

Referring still to FIG. 2, the gaseous effluent stream 522 may be passed to the product separator 540, which may be operable to separate the gaseous effluent stream 522 into at least one product stream 542 and at least one off-gas stream 544. The off-gas stream 544 recovered from the product separator 540 of the FCDh process 502 may include at least 40 mol %, at least 70 mol %, at least 75 mol %, at least 80 mol %, at least 85 mol %, or even at least 90 mol % hydrogen based on the total molar flow rate of the off-gas stream 544. The off-gas stream 544 may also include methane, nitrogen, and/or other constituents. At least a portion of the off-gas stream 544 recovered from the product separator 540 may be passed to the combustor 350 as at least a portion of the supplemental fuel stream 356. In some embodiments, the off-gas stream 544 may be combined with a secondary fuel stream 358 to produce the supplemental fuel stream 356. In some embodiments, the secondary fuel stream 358 may be a hydrogen-containing stream having a greater concentration of hydrogen than the off-gas stream 544. In other embodiments, the secondary fuel stream 358 may be a hydrocarbon stream comprising one or more hydrocarbons, such as methane or natural gas for example. In some embodiments, the flow rate of the secondary fuel stream 358, the flow rate of the off-gas stream 544, or both may be increased or decreased to increase or decrease the weight ratio of catalyst to hydrocarbon in the combustor 350.

The FCDh process 502 may also include a catalyst recycle stream 536 for recycling the reactivated catalyst 532 back to the combustor 350 of the FCDh process 502. In some embodiments, the supplemental fuel stream 356 that includes at least a portion of the off-gas stream 544 may have a fixed composition. The catalyst recycle stream 536 may, therefore, be modified to adjust the weight ratio of the catalyst to hydrocarbon in the combustor 350.

Figure 3:
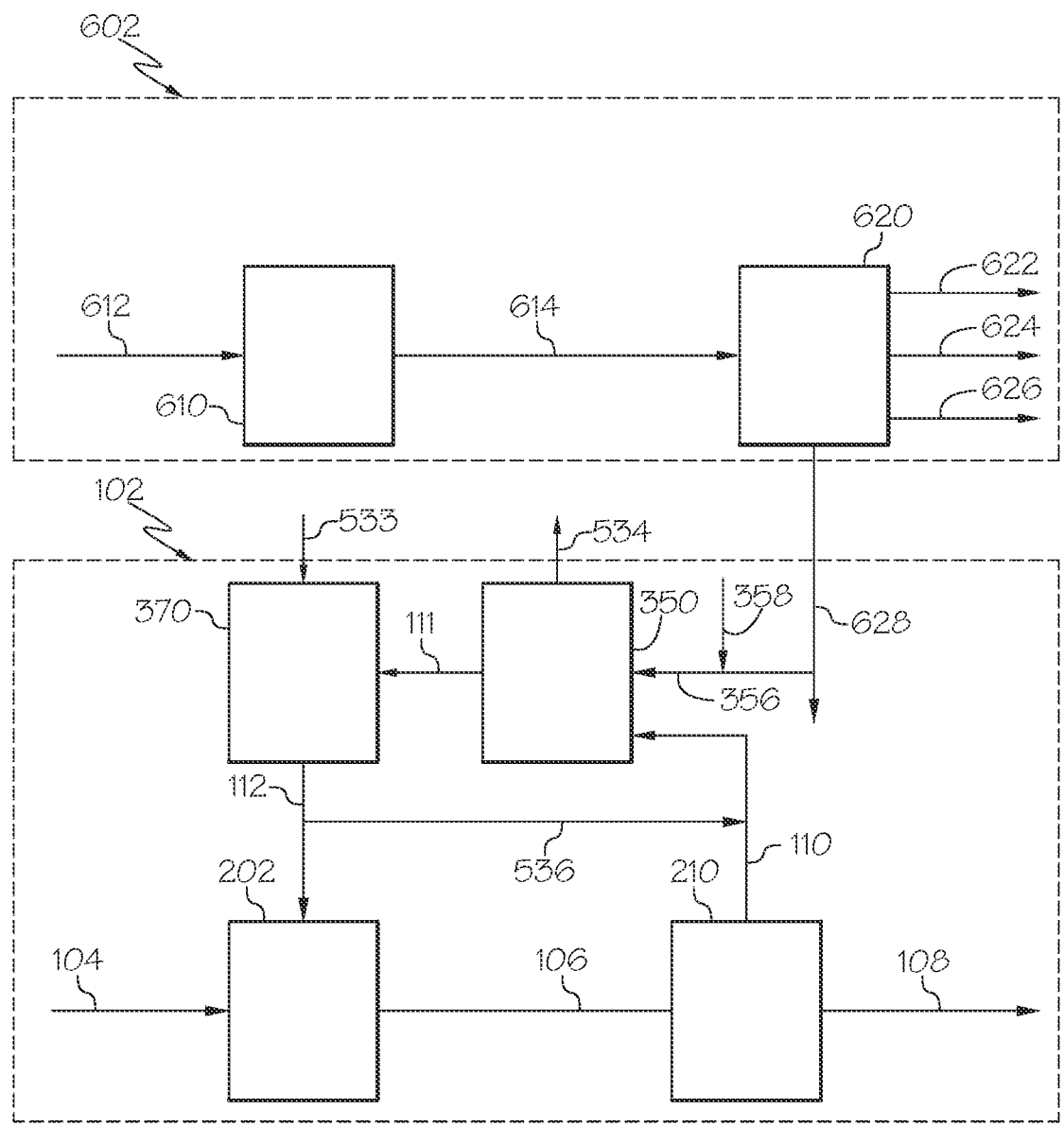
FIG. 3 schematically depicts another reactor system flow chart, according to one or more embodiments described herein.

Referring now to FIG. 3, a process flowchart depicts an embodiment in which a cracker off-gas stream 628 from a light hydrocarbon cracking process 602 may be passed to the combustor 350 of the reactor system 102 as at least a portion of the supplemental fuel stream 356. As previously discussed, the reactor system 102 can include the reactor 202, the catalyst separation section 210, the combustor 350, and the oxygen treatment zone 370. In continuous operation, a chemical feed 104 and a reactivated catalyst 112 from the oxygen treatment zone 370 may be introduced to the reactor 202, in which contact of the reactivated catalyst 112 with reactants in the chemical feed 104 may convert at least a portion of reactants in the chemical feed 512 to one or more reaction products. A reactor effluent 106 may be passed from the reactor 202 to the catalyst separation section 210, in which the reactor effluent 106 may be separated into a gaseous effluent stream 108 and a deactivated catalyst stream 110. The gaseous effluent stream 108, which may include at least one reaction product, may be passed to one or more downstream operations for further processing. The deactivated catalyst stream 110 may be passed to the combustor 350 for at least a portion of the catalyst processing. In the combustor 350, the supplemental fuel stream 356 may be combusted in the presence of the deactivated catalyst stream 110 to remove coke from the catalyst, heat the catalyst, or both. Following combustion, the heated catalyst 111 may be separated from the combustion gases 534 and passed from the combustor 350 to the oxygen treatment zone 370. In the oxygen treatment zone 370, the heated catalyst 111 may be treated with an oxygen-containing gas 533 to produce the reactivated catalyst 112. The reactivated catalyst 112 may then be passed back to the reactor 202.

Referring still to FIG. 3, the light hydrocarbon cracking process 602 may include a light hydrocarbon cracking unit 610 and a light hydrocarbon processing portion 620. During continuous operation of the light hydrocarbon cracking process 602, one or a plurality of light hydrocarbon streams 612 may be introduced to the light hydrocarbon cracking unit 610, in which light hydrocarbons in the hydrocarbon streams 612 are cracked to produce a cracker effluent 614 that includes one or more reaction products. For example, in some embodiments, the light hydrocarbon cracking unit 610 may be a steam cracker and the light hydrocarbon streams 612 may include ethane and propane, which may be steam cracked in the steam cracker to produce at least ethylene. The cracker effluent 614 may be passed to the light hydrocarbon processing portion 620 of the light hydrocarbon cracking process 602. The light hydrocarbon processing portion 620 may include a plurality of unit operations, such as but not limited to vapor compression, separation, sulfur and carbon dioxide removal, drying, or other operations. The light hydrocarbon processing portion 620 may ultimately separate the cracker effluent 614 into a plurality of gaseous streams, such as but not limited to, an ethylene product stream 622, a propylene product stream 624, a propane stream 626, a cracker off-gas stream 628, and other streams.

The cracker off-gas stream 628 may include at least 40 mol % hydrogen, such as from 50 mol % to 90 mol % hydrogen. At least a portion of the cracker off-gas stream 628 may be passed to the combustor 350 of the reactor system 102 to be included as a portion of the supplemental fuel stream 356. For example, in some embodiments, the cracker off-gas stream 628 may be passed directly to the combustor 350 of the reactor system 102 as the supplemental fuel stream 356 so that the supplemental fuel stream 356 consists of or consists essentially of the cracker off-gas stream 628. In some embodiments, the cracker off-gas stream 628 may be combined with a secondary fuel stream 358 to produce the supplemental fuel stream 356. The secondary fuel stream 358 may be a hydrogen-containing stream having a greater concentration of hydrogen than the cracker off-gas stream 628. Alternatively, in some embodiments, the secondary fuel stream 358 may be a hydrocarbon stream comprising one or more hydrocarbons. In some embodiments, the flow rate of the secondary fuel stream 358, the flow rate of the cracker off-gas stream 628, or both may be increased or decreased to increase or decrease the weight ratio of catalyst to hydrocarbon in the combustor 350.

The reactor system 102 may also include the catalyst recycle stream 536 for recycling the reactivated catalyst 532 back to the combustor 350. In some embodiments, the supplemental fuel stream 356 that includes at least a portion of the cracker off-gas stream 628 may have a fixed composition. The flow rate of the catalyst recycle stream 536 may, therefore, be increased or decreased to adjust the weight ratio of the catalyst to hydrocarbon in the combustor 350. In some embodiments, at least a portion of the cracker off-gas stream 628 may be combined with an off-gas stream from the reactor system 102 (e.g., off-gas stream 544 from the FCDh process 502 of FIG. 2) to produce the supplemental fuel stream 356. The supplemental fuel stream 356 may include off-gas streams from other hydrocarbon processes. In some embodiments, the supplemental fuel stream 356 may include at least one of an off-gas from a FCDh process, a cracker off-gas from a light hydrocarbon cracking unit, a purity hydrogen stream, or combinations of these.

In some embodiments, the reactor system 102 and the light hydrocarbon cracking process 602 may be integrated together to combine separation of the product streams into a single system. For example, in some embodiments, the gaseous effluent stream 108 from the reactor system 102 may be combined with the cracker effluent 614 from the light hydrocarbon cracking unit 610, and the combined effluent stream (not shown) may be passed to the light hydrocarbon processing portion 620. Thus, in these embodiments, the light hydrocarbon processing portion 620 may separate the combined effluent stream (e.g., the combination of both the gaseous effluent stream 108 and cracker effluent 614) into a plurality of gaseous streams, such as but not limited to, the ethylene product stream 622, the propylene product stream 624, the propane stream 626, the cracker off-gas stream 628, and other streams. In particular, in some embodiments, the gaseous effluent stream 522 (FIG. 2) from the FCDh process 502 (FIG. 2) may be combined with the cracker effluent 614 of the light hydrocarbon cracking process and may be passed therewith to the light hydrocarbon processing portion 620 of the light hydrocarbon cracking process 602 so that the cracker off-gas stream 628 includes off-gases produced from the light hydrocarbon cracking unit 610 and the FCDh process 502 (FIG. 2).

Figure 4:
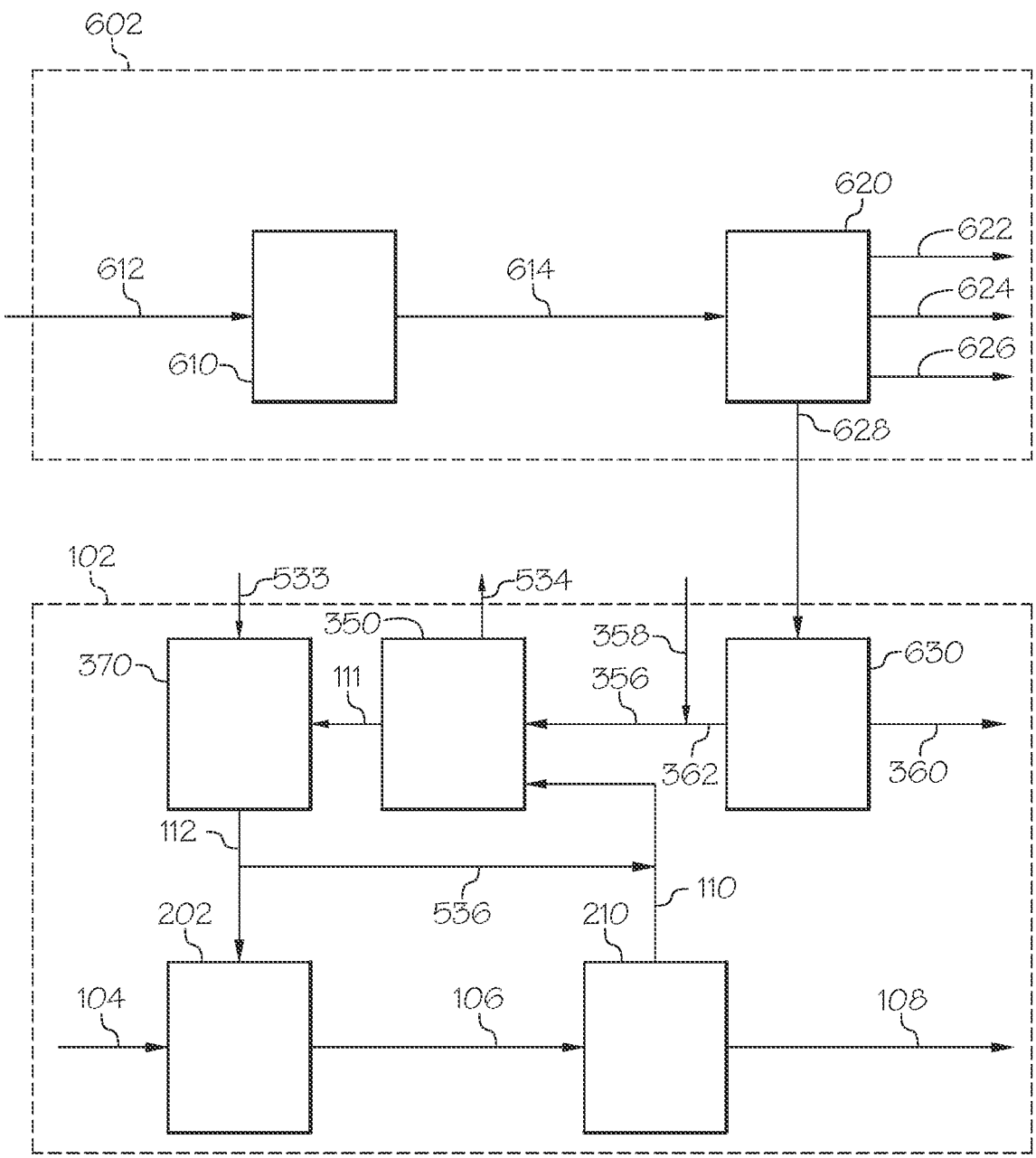
FIG. 4 schematically depicts yet another reactor system flow chart, according to one or more embodiments described herein.

Referring to FIG. 4, in some embodiments, the cracker off-gas stream 628 may be passed to a separator device 630, such as a turbo expander or other separation device. The separator device 630 may be operable to separate the cracker off-gas stream 628 into a hydrogen-rich stream 362 and a hydrocarbon-rich stream 360. The hydrogen-rich stream 362, the hydrocarbon-rich stream 360, or both may be passed from the separator device 630 to the combustor 350 of the reactor system 102 as at least a portion of the supplemental fuel stream 356. In some embodiments, the supplemental fuel stream 356 may include the hydrogen-rich stream 362 from the separator device 630. Off-gas streams from other hydrocarbon processing systems (e.g., off-gas stream 544 from the FCDh process 502 of FIG. 2) may also be passed to a separator device 630 to produce a hydrogen-rich stream and a hydrocarbon-rich stream and then passing at least the hydrogen-rich stream to the combustor 350 as a part of the supplemental fuel stream 356. In some embodiments, the operating parameters of the separator device 630 may be modified to increase or decrease a concentration of hydrocarbons in the supplemental fuel stream 356 to thereby increase or decrease the weight ratio of catalyst to hydrocarbon in the combustor 350.

During the continuous reaction phase of operation of the reactor system 102, the catalyst processing portion 300 of the reactor system 102, in particular the combustor 350, may be maintained at a temperature in an operating temperature range sufficient to reactivate the catalyst. For example, in some embodiments, the combustor 350 may be maintained at a temperature greater than the operating temperature of the reactor portion 200 of the reactor system 102. In some embodiments, the operating temperature range of the combustor 350 may be greater than or equal to 650° C., greater than or equal to 660° C., even greater than or equal to 680° C., or even greater than or equal to 700° C. In some embodiments, the operating temperature range of the combustor 350 may be from 650° C. to 850° C., from 660° C. to 780° C., or from 700° C. to 750° C. As previous discussed herein, maintaining the operating temperature in the combustor 350 may include combusting a supplemental fuel in the combustor 350.

Referring again to FIG. 1, the supplemental fuel stream 356 may be introduced to the combustor 350 of the catalyst processing portion 300. In some embodiments, the supplemental fuel stream 356 may be introduced to the combustor 350 through one or more distributors (not shown) disposed within the combustor 350. Before introducing the supplemental fuel stream 356 to the combustor 350, the supplemental fuel stream 356 may be passed through a compressor (not shown) to increase the pressure of the supplemental fuel stream 356. The supplemental fuel stream 356 can be supplied to the combustor 350 at a pressure of from 5 pounds per square inch gauge (psig) to 200 psig (from 34.47 kilopascals (kPa) to 1378.95 kPa, where 1 psig=6.89 kPa). In some embodiments, a control valve (not shown) may be included to control the flow rate of the supplemental fuel stream 356 and adjust the pressure of the supplemental fuel gas to equal the operating pressure of the reactor system 102 and/or the combustor 350. In some embodiments, the supplemental fuel stream 356 may be preheated, such as by passing the supplemental fuel stream 356 through an optional heat exchanger (not shown).

According to one or more embodiments, the reaction in the reactor system 102 may be a FCDh reaction system for dehydrogenating paraffins and alkyl aromatics to olefins or other products. According to such embodiments, the feed stream may comprise paraffinic compounds such as one or more of ethane, propane, n-butane, i-butane. In some embodiments, the feed stream may include at least 50 wt. % ethane, propane, n-butane, i-butane, or combinations thereof. In one or more embodiments, a dehydrogenation reaction may utilize a catalyst that includes platinum, gallium, or combinations thereof. The platinum and/or gallium may be carried by an alumina or alumina silica support, and may optionally comprise potassium. Such platinum catalysts are disclosed in U.S. Pat. No. 8,669,406, which is incorporated herein by reference in its entirety. In some embodiments, the reactor system 102 may be a FCDh reaction system for dehydrogenating alkyl aromatic compounds to other products. For example, the feed stream may include ethylbenzene and the reactor system 102 may be a FCDh reactor system for dehydrogenating the ethylbenzene to styrene.

EXAMPLES

Embodiments of the present disclosure will be further clarified by the following non-limiting examples.

Example 1: Effect of Weight Ratio of Catalyst to Hydrocarbon on Conversion of Propane Dehydrogenation Reactions at Relatively Low Heat Input In Example 1, the effects of increasing the weight ratio of catalyst to hydrocarbon in the combustor on the conversion of propane in a propane dehydrogenation reactor system were evaluated during operation of the reactor system at relatively low heat input. The propane dehydrogenation reactions were conducted using a Davidson Circulating Riser (DCR) pilot plant unit obtained from Grace Davidson and having an upflow fluidized reactor portion and a catalyst processing portion. The DCR unit was modified to allow in-situ fuel combustion in the catalyst processing portion. Each reaction run 1A-1D was conducted with 4100 grams of freshly loaded catalyst comprising platinum and gallium supported on a silica-containing alumina carrier. The inlet temperature to the riser reactor of the DCR unit was controlled at 630° C. and the pressure was set to 13 psig. The propane feed was an HD-5 propane feed with around 30 parts per million (ppm) sulfur on a molar basis. The propane feed was diluted in nitrogen so that the partial pressure of propane in the feed stream was about 4.3 psig.

The temperature for catalyst processing was maintained in a range of from 700° C. to 750° C. Catalyst processing included combustion of a supplemental fuel stream followed by an oxygen treatment in which the catalyst was exposed to an oxygen-containing gas (air) for an oxygen soak time. For reaction runs 1A-1E, the weight ratios of catalyst to hydrocarbon in the catalyst processing portion were adjusted by changing the molar concentration of methane in the supplemental fuel stream. The flow rate of the supplemental fuel stream was increased with decreasing methane concentration to maintain operation of the reactor system at a constant heat input of about 1,600 BTU/hour (1.6 KBTU/hr), referred to these Examples as low heat input. For each reaction run, the DCR unit was operated for a first period with an oxygen soak time of 1 minute and for a second period with an oxygen soak time of 7 minutes.

The propane feed rate (standard liters per hour (SLPH)), catalyst circulation rate (kg/hr), supplemental fuel stream composition (mol % and wt. %), supplemental fuel stream feed rate (SLPH), heat input (MBTU/hr), ratio of catalyst to methane (lbs/lbs) in the catalyst processing portion, propane weight hourly space velocity (WHSV $hr^{-1}$), and oxygen soak time of the oxygen treatment are provided below in Table 1. The catalyst circulation rates in Examples 1 and 2 refer to the rates at which the catalyst is circulated between the reactor portion and the catalyst processing portion. The propane conversions for operation of the reactor system with oxygen soak times of 1 minute and 7 minutes were determined and reported in Table 1.

TABLE 1

| Example 1 Process Parameters and Propane Conversion | | | | | |
|---|---|---|---|---|---|
| Reaction Run | 1A | 1B | 1C | 1D | 1E |
| Supplemental Fuel Composition | | | | | |
| Methane (mol %) | 100 | 75 | 20 | 11 | 0 |
| Hydrogen (mol %) | 0.01 | 25 | 80 | 89 | 100 |
| Reaction Process Parameters | | | | | |
| Propane Feed Rate (SLPH) | 180 | 180 | 180 | 180 | 180 |
| Propane WHSV ($hr^{-1}$) | 4.5 | 4.4 | 3.6 | 4.1 | 3.7 |
| Catalyst Circ. Rate (kg/hr) | 18.6 | 19.5 | 20.2 | 20.0 | 19.5 |
| Supplemental Fuel Rate (SLPH) | 50 | 61 | 113 | 131 | 164 |
| Heat Input (KBTU/hr) | 1.57 | 1.57 | 1.56 | 1.55 | 1.54 |
| Weight Ratio Catalyst/Methane in Combustor (lbs/lbs) | 561:1 | 643:1 | 1349:1 | 2095:1 | >2500:1* |

TABLE 1-continued

| Example 1 Process Parameters and Propane Conversion | | | | | |
|---|---|---|---|---|---|
| Reaction Run | 1A | 1B | 1C | 1D | 1E |
| Propane Conversion | | | | | |
| Propane Conversion (%)-oxygen soak time of 1 minute | 42.1 | 42.9 | 45.7 | 44.6 | 48.2 |
| Propane Conversion (%)-oxygen soak time of 7 minutes | 43.2 | 43.9 | 45.8 | 45.3 | 49.1 |

*1E having supplemental fuel comprising 0 mol % methane represents the upper theoretical limit of the weight ratio of catalyst to methane As shown in Table 1, for Example 1, the propane conversion with 1 minute of oxygen soak time is observed to increase from 42.1% to 44.6% when the weight ratio of catalyst to methane in the catalyst processing portion is increased from 561:1 (1A) to 2095:1 (1D). Thus, increasing the weight ratio of catalyst to hydrocarbon in the catalyst processing portion from 561:1 to 2095:1 increased the propane conversion by 6%. As the weight ratio of catalyst to methane in the combustor of the catalyst processing portion is further increased above 2095:1, such as greater than 2500:1 as in example 1E, the propane conversion levels off at a theoretical maximum propane conversion of near 50%. For example, increasing the catalyst to methane weight ratio in the combustor from 561:1 (1A) to the theoretical limit (1E) results in an increase in the propane conversion of from 42.1% to 48.2% (oxygen soak time of 1 min.), which is an increase of about 14.5%.

Example 2: Effect of Weight Ratio of Catalyst to Hydrocarbon on Conversion of Propane Dehydrogenation Reactions at Relatively High Heat Input In Example 2, the effects of increasing the weight ratio of catalyst to hydrocarbon in the catalyst processing portion on the propane conversion of a propane dehydrogenation reactor system operating at relatively high heat input (i.e., 3 times the supplemental fuel flow rate of Example 1) were evaluated. The propane dehydrogenation reactions were conducted in the DCR unit described in Example 1. In Example 2, the catalyst processing was conducted at relatively high heat input which was accomplished by increasing the supplemental fuel stream flow rate to 3 times the supplemental fuel stream flow rate of Example 1. The propane dehydrogenation reactions were conducted at constant heat input of about 4,700 BTU/hour (4.7 KBTU/hr). All other operating parameters were the same. The propane dehydrogenation reactions were conducted using supplemental fuel streams comprising hydrogen and methane. For reaction runs 2A-2E, the weight ratios of catalyst to hydrocarbon in the catalyst processing portion were adjusted by changing the molar concentration of methane in the supplemental fuel stream. The flow rate of the supplemental fuel stream was increased with decreasing methane concentration to maintain operation of the reactor system at a constant heat input. The propane feed rate, catalyst circulation rate, supplemental fuel stream composition, supplemental fuel stream feed rate, heat input, ratio of catalyst to methane in the catalyst processing portion of the reaction system, propane WHSV, and oxygen soak time of the oxygen treatment are provided below in Table 2. The propane conversions for operation of the reactor system with oxygen soak times of 1 minute and 7 minutes were determined and reported in Table 1.

TABLE 2

Example 2 Process Parameters and Propane Conversion

| Reaction Run | 2A | 2B | 2C | 2D | 2E |
|---|---|---|---|---|---|
| Supplemental Fuel Composition | | | | | |
| Methane (mol %) | 100 | 75 | 20 | 11 | 0 |
| Hydrogen (mol %) | 0.01 | 25 | 80 | 89 | 100 |
| Reaction Process Parameters | | | | | |
| Propane Feed Rate (SLPH) | 192 | 180 | 180 | 180 | 180 |
| Propane WHSV (hr$^{-1}$) | 5.4 | 3.7 | 3.2 | 3.5 | 3.8 |
| Catalyst Circ. Rate (kg/hr) | 18.0 | 20.0 | 20.2 | 20.0 | 20.1 |
| Supplemental Fuel Rate (SLPH) | 150 | 182 | 338 | 393.3 | 394.3 |
| Heat Input (KBTU/hr) | 4.71 | 4.72 | 4.67 | 4.66 | 3.71 |
| Weight Ratio Catalyst/Methane in Combustor (lbs/lbs) | 181:1 | 221:1 | 451:1 | 698:1 | >2500:1* |
| Propane Conversion | | | | | |
| Propane Conversion (%)-oxygen soak time of 1 minute | 34.9 | 37.2 | 44.0 | 42.0 | 48.5 |
| Propane Conversion (%)-oxygen soak time of 7 minutes | 37.7 | 43.1 | 47.0 | 44.8 | 49.1 |

*2E having supplemental fuel comprising 0 mol % methane represents the upper theoretical limit of the weight ratio of catalyst to methane As shown in Table 2, for the propane dehydrogenations Example 2 conducted at relatively high heat input, the propane conversion with 1 minute of oxygen soak time is observed to increase from 34.9% to 42.0% when the weight ratio of catalyst to methane in the catalyst processing portion is increased from 181:1 (2A) to 698:1 (2D). Thus, at the relatively higher heat input, increasing the weight ratio of catalyst to hydrocarbon in the catalyst processing portion from 181:1 to 698:1 increased the propane conversion by 20%. As the weight ratio of catalyst to methane in the combustor of the catalyst processing portion is further increased above 698:1, such as greater than 2500:1 as in example 2E, the propane conversion levels off at a theoretical maximum propane conversion of near 50%. For example, increasing the catalyst to methane weight ratio in the combustor from 181:1 (2A) to the theoretical limit (2E) results in an increase in the propane conversion of from 34.9% to 48.5% (oxygen soak time of 1 min.), which is an increase of about 39%.

Figure 5:
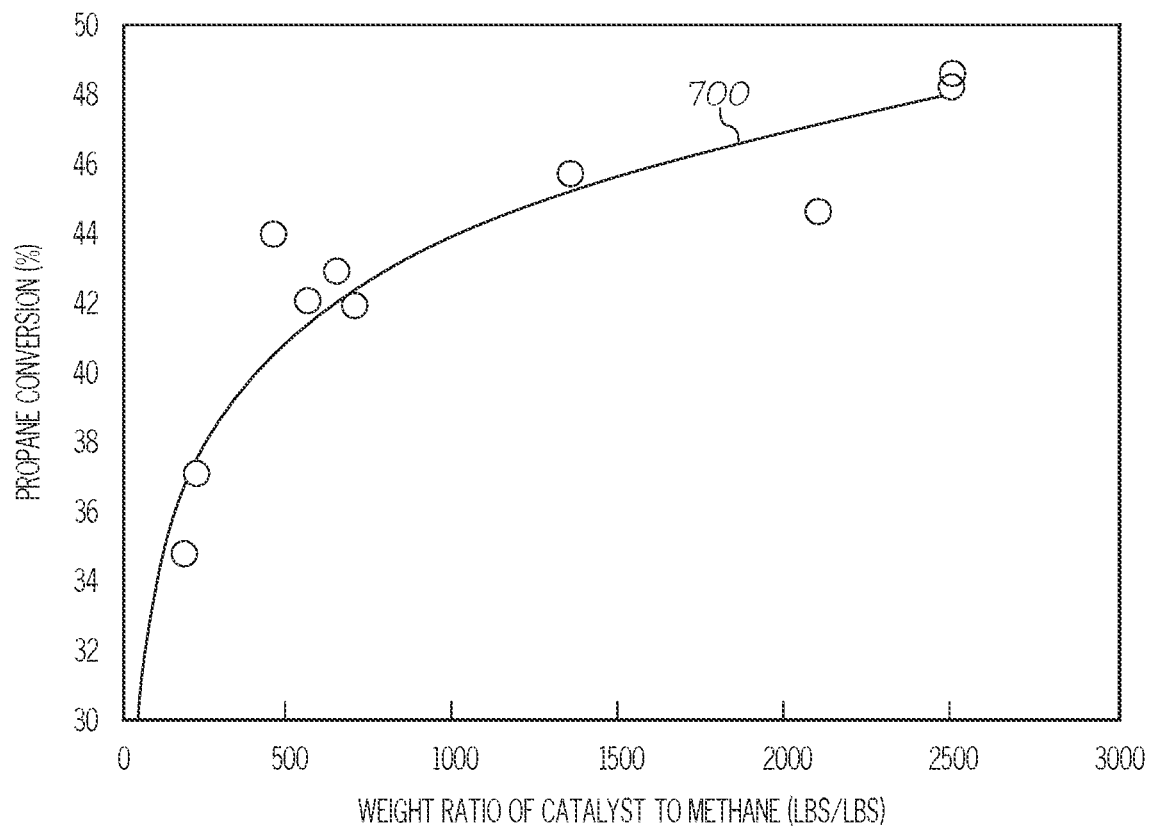
FIG. 5 schematically depicts a graph of propane conversion (y-axis) as a function of the weight ratio of catalyst to methane in the combustor (x-axis) for a fluidized catalytic dehydrogenation reactor system in which the supplemental fuel stream includes methane and/or hydrogen, according to one or more embodiments described herein.

Referring to FIG. 5, propane conversion (%) (y-axis) (700) is shown graphically as a function of the weight ratio of catalyst to methane in the catalyst processing portion (x-axis) for the propane dehydrogenations of Examples 1 and 2. As shown graphically in FIG. 5, the propane conversion 700 increases as the weight ratio of catalyst to methane in the catalyst processing portion increases given that the total heat input to the reactor system is held constant.

As shown in FIG. 5, the propane conversion increases rapidly when the weight ratio of catalyst to methane in the catalyst processing portion is increased up to about 300:1. In other words, below a catalyst to methane weight ratio of 300:1, the propane conversion decreases rapidly. Therefore, operating the reactor system with a catalyst to hydrocarbon weight ratio in the catalyst processing portion of greater than or equal to 300:1 provides superior performance compared to operating the reactor system with a catalyst to hydrocarbon weight ratio of less than 300:1. As the weight ratio of catalyst to methane in the catalyst processing portion is increased above 300:1, such as from 300:1 to 2500:1, the rate of increase in the propane conversion becomes slower and eventually reaches a plateau level at slightly less than 50% conversion, at which point the amount of methane (hydrocarbon) in the catalyst processing portion is negligible. In FIG. 5, a catalyst to methane weight ratio of about 2500:1 is assumed to represent an infinitely large weight ratio corresponding to no methane in the catalyst processing portion (e.g., no methane or other hydrocarbons in the supplemental fuel stream). The propane dehydrogenations of Examples 1 and 2 demonstrate that increasing the weight ratio of catalyst to hydrocarbon in the catalyst processing portion to greater than or equal to 300:1, or even greater than or equal to 500:1 can substantially increase the propane conversion of the reactor system.

For the purposes of describing and defining the present invention it is noted that the term "about" is utilized herein to represent the inherent degree of uncertainty that may be attributed to any quantitative comparison, value, measurement, or other representation. The term is also utilized herein to represent the degree by which a quantitative representation may vary from a stated reference without resulting in a change in the basic function of the subject matter at issue.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

Generally, "inlet ports" and "outlet ports" of any system unit of the reactor system 102 described herein refer to openings, holes, channels, apertures, gaps, or other like mechanical features in the system unit. For example, inlet ports allow for the entrance of materials to the particular system unit and outlet ports allow for the exit of materials from the particular system unit. Generally, an outlet port or inlet port will define the area of a system unit of the reactor system 102 to which a pipe, conduit, tube, hose, material transport line, or like mechanical feature is attached, or to a portion of the system unit to which another system unit is directly attached. While inlet ports and outlet ports may sometimes be described herein functionally in operation, they may have similar or identical physical characteristics, and their respective functions in an operational system should not be construed as limiting on their physical structures.

It will be apparent to those skilled in the art that various modifications and variations can be made to the present invention without departing from the spirit and scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

The invention claimed is:

1. A method for processing a feed stream to produce a product stream, the method comprising:
   contacting the feed stream with a catalyst in a reactor portion of a reactor system, wherein:

the reactor system comprises a fluidized catalytic reactor system having a reactor portion and a catalyst processing portion;

the catalyst comprises at least one active metal; and the contacting of the feed stream with the catalyst causes a dehydrogenation reaction which forms an effluent stream comprising one or more olefins, alkyl aromatics, or both;

separating at least a portion of the effluent stream from the catalyst;

passing the catalyst to the catalyst processing portion of the reactor system;

processing the catalyst in the catalyst processing portion of the reactor system, wherein processing the catalyst comprises:

passing the catalyst to a combustor of the catalyst processing portion;

combusting a supplemental fuel stream in the combustor to heat the catalyst, wherein the supplemental fuel stream comprises one or more hydrocarbons and greater than or equal to 50 mol % hydrogen; and passing the heated catalyst from the catalyst processing portion to the reactor portion of the reactor system.

2. The method of claim 1, wherein a weight ratio of the catalyst to the one or more hydrocarbons in the combustor is at least 300:1.

3. The method of claim 1, wherein the one or more hydrocarbons is chosen from methane, ethane, propane, n-butane, isobutane, ethylene, propylene, 1-butene, 2-butene, isobutene, pentene, benzene, toluene, xylene, natural gas, or combinations thereof.

4. The method of claim 1, wherein the supplemental fuel stream comprises a process stream comprising one or more hydrocarbons.

5. The method of claim 4, wherein the process stream is an off-gas stream recycled from the reactor system or a hydrocarbon-containing off-gas stream from another hydrocarbon processing system.

6. The method of claim 1, wherein the supplemental fuel stream comprises at least 1 mol % of the one or more hydrocarbons.

7. The method of claim 1, comprising maintaining the weight hour space velocity (WHSV) of the supplemental fuel stream in the combustor so that the WHSV does not change by more than 5% over an hour of time-on-stream.

8. The method of claim 1, further comprising treating the heated catalyst with an oxygen-containing gas to produce a reactivated catalyst and passing the reactivated catalyst from the catalyst processing portion to the reactor portion, wherein treating the heated catalyst with an oxygen-containing gas comprises exposing the heated catalyst to an oxygen-containing gas for a time period of greater than 2 minutes.

9. The method of claim 1, further comprising recycling at least a portion of the heated catalyst back to the combustor of the catalyst processing portion to control the weight ratio of the catalyst to the one or more hydrocarbons in the combustor.

10. The method of claim 9, further comprising modifying the weight ratio of the catalyst to the one or more hydrocarbons in the combustor by increasing or decreasing a proportion of the heated catalyst recycled back to the combustor.

11. The method of claim 9, further comprising maintaining a constant heating value of the supplemental fuel stream.

12. The method of claim 1, wherein the supplemental fuel stream comprises methane.

13. The method of claim 1, further comprising:

separating the effluent stream into a product stream and an off-gas stream; and passing at least a portion of the off-gas stream to the catalyst processing portion, wherein the supplemental fuel stream includes the at least a portion of the off-gas stream.

14. The method of claim 1, wherein the active metal comprises one or more metals from groups 9 and 10 of the IUPAC periodic table.

15. The method of claim 1, wherein the catalyst comprises a metal selected from the group consisting of platinum, gallium, palladium, rhenium, iridium, indium, germanium, and combinations of these.

16. The method of claim 15, wherein the catalyst further comprises an alkali metal or alkaline earth metal supported on a carrier, the carrier chosen from one or more of silica, alumina, silica-containing alumina, $TiO_2$, $ZrO_2$, or combinations of these.

17. The method of claim 1, wherein the reactor system comprises a fluidized catalytic dehydrogenation reactor system.

* * * * *